United States Patent [19]

Mollo

[11] Patent Number: 4,632,099
[45] Date of Patent: Dec. 30, 1986

[54] EMERGENCY TRANSPORT NECK IMMOBILIZER

[76] Inventor: Leonard J. Mollo, Rte. 1, Box 1, Highway 20, Lumberbridge, N.C. 28357

[21] Appl. No.: 692,379

[22] Filed: Jan. 17, 1985

[51] Int. Cl.$^4$ .......................... A61F 5/02; A61F 5/04; A61H 3/00
[52] U.S. Cl. .................................... 128/87 B; 128/75; 128/78
[58] Field of Search .............. 128/75, 78, 87 B, 84 R, 128/84 C, 85, DIG. 20, DIG. 23

[56] References Cited

U.S. PATENT DOCUMENTS

| | | | |
|---|---|---|---|
| 757,140 | 4/1904 | Neffeler | 128/78 |
| 1,316,915 | 9/1919 | Meyer et al. | 128/78 |
| 2,642,864 | 6/1953 | Ward | 128/75 |
| 2,706,982 | 4/1955 | Hale et al. | 128/87 B |
| 2,813,527 | 11/1957 | Cook | 128/87 B |
| 2,828,737 | 4/1958 | Hale | 128/78 |
| 3,605,736 | 9/1977 | D'Amico et al. | 128/75 |
| 3,795,243 | 3/1974 | Miller | 128/75 |
| 3,915,161 | 10/1975 | Shields | 128/75 |
| 4,015,597 | 5/1977 | Beaver | 128/75 |
| 4,161,946 | 7/1979 | Zuesse | 128/75 |
| 4,250,874 | 2/1981 | Rude | 128/75 |
| 4,539,979 | 9/1985 | Bremer | 128/75 |

FOREIGN PATENT DOCUMENTS

| | | | |
|---|---|---|---|
| 980199 | 12/1975 | Canada | 128/75 |
| 3302078 | 1/1983 | Fed. Rep. of Germany | 128/75 |

Primary Examiner—Richard J. Johnson
Assistant Examiner—Kathleen J. D'Arrigo
Attorney, Agent, or Firm—B. B. Olive

[57] ABSTRACT

An emergency transport neck immobilizing brace incorporates a frame structure adapted for mounting on the shoulders of a patient suspected of having a neck injury and securable to the body of the patient by both crotch and shoulder straps. The brace frame mounts a head halter with a two-point strap suspension arrangement and a ratchet mechanism for placing the patient's head in traction. Cushion devices are also provided to limit both forward and backward and lateral movement of the patient's head after being placed in traction.

8 Claims, 7 Drawing Figures

EMERGENCY TRANSPORT NECK IMMOBILIZER

TECHNICAL FIELD

The invention relates broadly to braces for the human body and more specifically to an emergency and temporary brace for immobilizing a patient's neck.

BACKGROUND ART

It has long been the practice in the medical art to brace the neck of a person suspected of having or known to have a neck or cervical spine injury. Often it is desirable to apply such a brace prior to moving the injured person from the scene of the accident causing the suspected or known injury. An emergency in-transit neck immobilizing brace, sandbags, board, or the like, applied at the scene of the accident is often and necessarily replaced by another brace, once the patient reaches the hospital and has gone through emergency examination and diagnostic procedures. In emergency use, certain basic characteristics are required for the brace which do not necessarily apply to the type of brace applied to the patient in the hospital environment.

While various attempts have been made in the past to provide a neck brace particularly suited and intended solely for emergency transport and the initial emergency treatment and examination of a patient often including X-ray examination, no such brace has come into widespread use. In what is believed to represent the closest prior art, there was described in a patent application filed Sept. 23, 1981, Ser. No. 304,961, entitled "Cervical Stabilizer Means" by Donald C. Truesdale, a brace having a frame structure which mounts on the shoulders of the patient and is secured by a pair of arm straps and a torso encircling belt. While the construction of the Truesdale brace is believed to represent a significant advance over the art preceding the invention of the Truesdale brace, the Truesdale brace, so far as applicant is knowledgable, has not gone into production and use. Among the characteristics of the Truesdale brace which the present invention brace seeks to avoid is the need for use of a torsion wrench to place the head in suspension. The present invention also seeks to avoid use of a single suspension for the head halter and use of a torso belt. Unlike the invention brace, the Truesdale brace also lacks means to prevent forward and back and lateral swinging of the head relative to the brace and lacks means for securing the brace to the crotch of the patient. Advantageously, the Truesdale brace does employ radioluscent frame material permitting X-ray examination.

The prior art related to body braces is otherwise voluminous. Therefore, only selected prior patents will be mentioned as being representative of approaches taken in the past. U.S. Pat. Nos. 2,642,864, 3,605,736, 3,795,243, 4,194,501, and 4,250,874 represent shoulder-supported braces with adjustable means for placing the head in traction. U.S. Pat. Nos. 3,507,273 and 4,161,946 represent other types of braces which rest on the body in a self-securing manner.

With all of the aforementioned prior art in mind, the present invention seeks to provide a brace primarily intended for use only during emergency transport of an individual suspected of having a neck injury, whether by air, sea, or land emergency transport. More specifically, the object of the invention is to provide such a brace which is light in weight, is easy and quick to install, is designed so as not to interfere with the initial treament through emergency care including possible X-ray and cardiology examinations, is stable on the body during transport, is designed to prevent forward and back and lateral movement of the head of the patient while held in traction, is comfortable to the patient during transport and is also designed to leave the patient mobile in the absence of leg injuries and in those situations in which the patient is able to walk once the patient's neck has been braced.

The foregoing and other objects will become apparent as the description proceeds.

DISCLOSURE OF INVENTION

The invention brace comprises a frame made up of radiotranslucent, i.e., translucent to X-ray, members. A pair of laterally-spaced, inverted U-shaped frame members constituting an upper frame are joined at the bottom by another pair of inverted J-shaped members constituting a lower frame and providing shoulder supports and back rest structure. Crotch straps and underarm straps secure the lower frame of the invention brace to the body. A ratchet-operated bar on the upper frame suspends by a pair of laterally-spaced straps a spring-loaded head halter which places the head in traction. More substantial limiting of forward and backward as well as lateral movement of the patient's head is assured by means of a pair of adjustable, curved cushions which partially surround and press against the sides of the head to limit such travel.

BEST MODE FOR CARRYING OUT THE INVENTION

Figure 1:
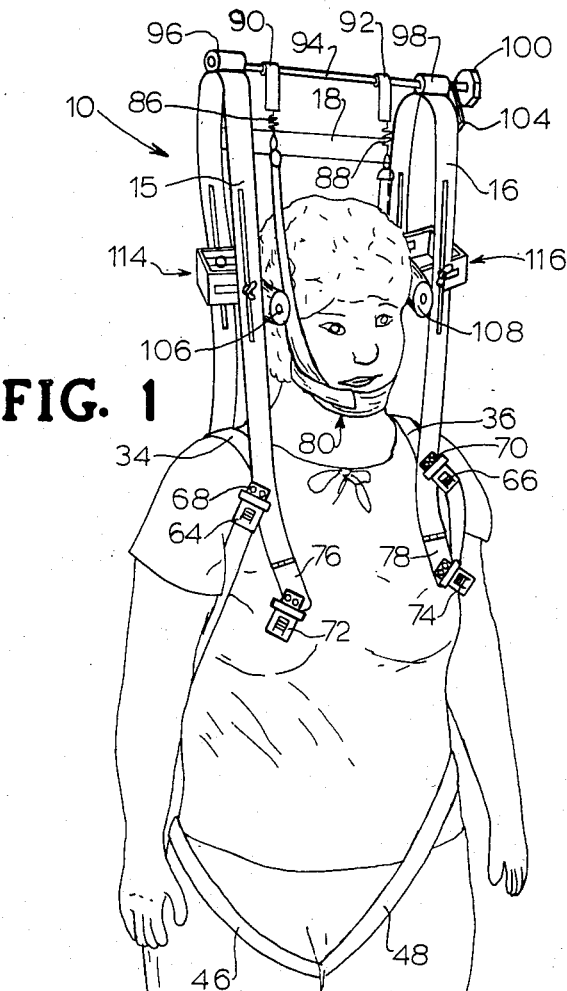
FIG. 1 is a perspective front view of a patient wearing a brace according to the invention and with head cushions.
Figure 2:
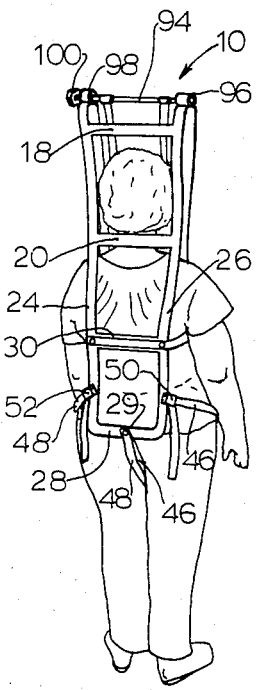
FIG. 2 is a perspective back view of a patient wearing a brace according to the invention but without head cushions.

The brace 10 of the invention comprises a frame structure preferably formed of plastic, radioluscent material which includes a pair of laterally-spaced inverted U-shaped frame members 15, 16 secured together by upper crossbar 18 and lower crossbar 20 on the back side of brace 10. Frame members 15, 16 while substantially parallel are angled slightly inwardly as viewed in the drawings whereas crossbars 18 and 20 are substantially parallel. With the brace 10 installed and the patient mobile as in FIG. 1, members 15, 16 extend upwardly from the patient's shoulders and bars 18, 20 extend generally horizontal and reside behind the patient's head forming what will be referred to as the upper immobilizing frame. Frame members 15, 16 are further joined together at the lower ends of frame members 15, 16 by a pair of inverted J-shaped, laterally-spaced shoulder and body-support members 24, 26 joined by lower crossbar 28 and upper crossbar 30. Support members 24, 26 with crossbars 28, 30 form a lower body securing frame. Inverted U-shaped sections 34, 36 rest on the patient's shoulders (FIG. 1) and suitably curved back rest sections 38, 40 terminate preferably immediately above the location of the pelvic bone with crossbar 28.

Crotch straps 46, 48 of adjustable length centrally and suitably secured to bar 28 by fastener 29 have female connectors 50, 52 snap-engagable with male connectors 54, 56 located on the rear and near the bottom of the lower frame. Underarm straps 60, 62 also of adjustable length fitted with female connectors 64, 66 attach, dependent on the patient's size, either to upper male connectors 68, 70 or lower male connectors 72, 74. Male connectors 72, 74 generally at nipple level mount on hinged tab sections 76, 78 to accommodate in a self-adjusting manner to a female patient having large breasts or to an obese male or female patient.

A conventional head halter 80 is secured by snap hooks 82, 84, springs 86, 88 and laterally-spaced straps 90, 92 to rotatable bar 94 in mounts 96, 98 on and integrally molded with members 15, 16. Bar 94 is operated by handle 100 and use of a suitable ratchet mechanism 102 having a releasable pawl 104. Thus, by tightening halter 80, the head of the patient can be brought into traction in a two-point suspension arrangement while allowing, through the provision of springs 86, 88, some mobility movement of the patient's chin. Springs 86, 88 also serve as some protection against overtightening of the ratchet mechanism 102.

Figure 6:
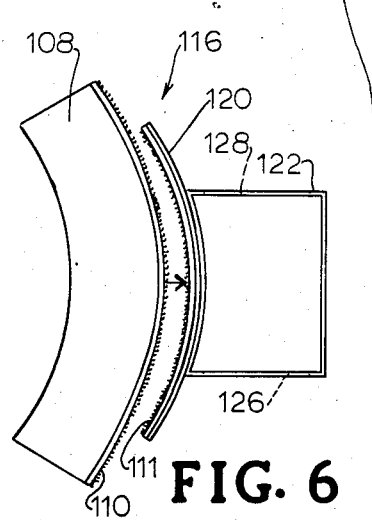
FIG. 6 is a plan view of one of the cushions and cushion supports used to limit forward and backward as well as lateral movement of the head when mounted on the invention brace with the cushion being shown detached from its support.
Figure 7:
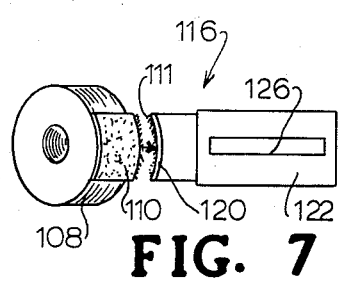
FIG. 7 is an end view of the cushion and cushion support shown in FIG. 5.
Figure 5:
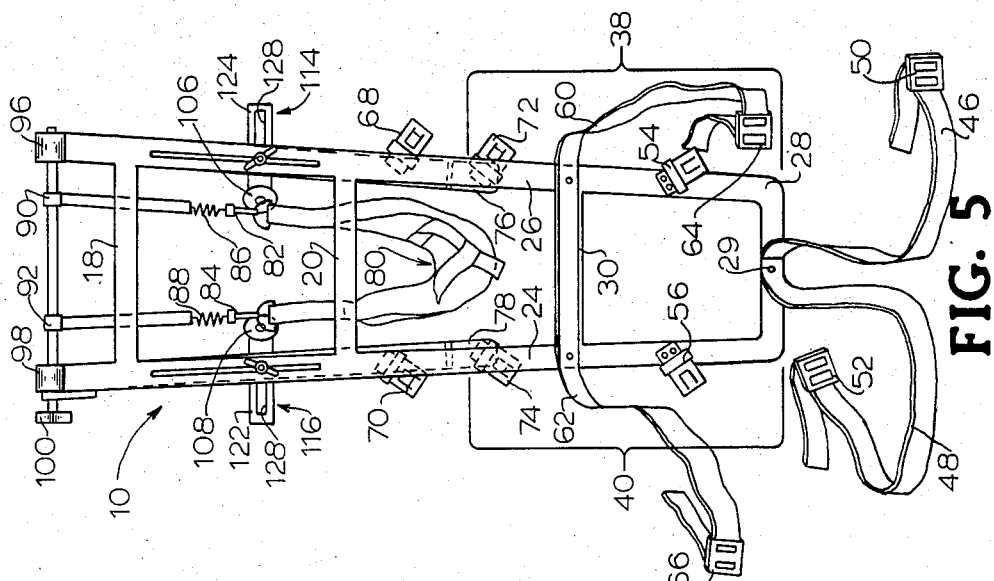
FIG. 5 is a back view of the invention brace.
Figure 4:
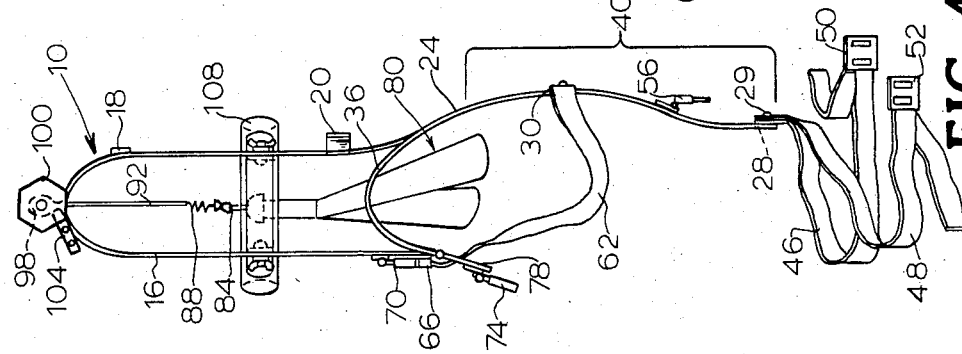
FIG. 4 is a side view of the invention brace.
Figure 3:
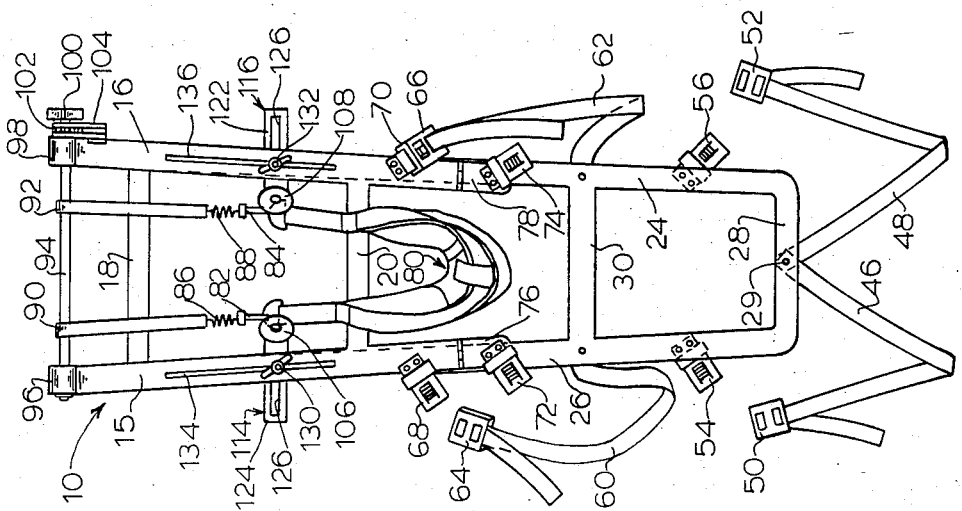
FIG. 3 is a front view of the invention brace.

In addition to providing means for placing the patient's head in traction, the invention brace 10 also, by means of the vertically, horizontally and angularly adjustable supports 114, 116 and tubular cushions 106, 108, provides means for comfortably but securely limiting forward and backward as well as lateral movement of the head of the patient once the patient's head has been suitably tractioned by means of the previously-described head halter mechanism. Cushions 106, 108 partially surround the patient's head and mount Velcro-type straps 110 which mate with other Velcro-type straps 111 on outwardly curved face plates 120 (FIGS. 5 and 6) on cushion supports 114, 116. The cushion supports 114, 116 mount the cushion-receiving, curved face plates 120 on U-shaped frames 122, 124, the sides of which are provided with horizontal front slots 126 and rear slots 128. Wing nut fastener bolts 130, 132 received by front slots 126 in turn are adjustably mounted in vertical slots 134, 136 formed in the front of brace members 15, 16. A comparable pair of wing nut fastener bolts are received by rear slots 128 as seen in FIG. 4. Thus, vertical, horizontal and angular adjustments of cushions 106, 108 can be achieved.

From the foregoing description, it will be understood that the lower frame of the brace is mounted on the patient as illustrated in FIG. 1 using the crotch straps 46, 48 and the underarm straps 60, 62 suitably lengthened, connected and tightened as illustrated in FIG. 1. Once so mounted on the patient, the lower frame of the brace is secured to the patient's body in a substantially stable but comfortable position. The head halter 80 on the upper frame of the brace 10 is suitably positioned under the patient's chin and is tightened by rolling up the pair of halter support straps 90, 92 on the ratchet-operated bar 94 until the patient's head is placed in appropriate traction. The cushion supports 114, 116 are then adjusted vertically, horizontally and angularly as required to hold the patient's head firmly and comfortably secured near the temples and in a manner so as to substantially prevent any forward and backward or lateral movement of the patient during transport and during any preliminary diagnostic and examination proceedings conducted during transport or at the hospital emergency room until a more suitable brace is substituted for the brace of the invention.

The invention brace 10, from the foregoing description, offers at least these advantages, all of which are obtained in the same brace construction:

1. A head halter suspension arrangement in which the head is supported in a two-point rather than in a single point suspension as in some of the prior art braces.

2. Means for placing the patient's head in traction by operating a manual handle not requiring use of any type of tool such as a torsion wrench, or the like.

3. Means for comfortably preventing both back and forth as well as lateral swinging of the head during transport.

4. Cushioned head secured means adapted to adjust in and out, up and down, and in an angular relation with respect to the head so as to accommodate to various head shapes as well as various accident situations.

5. A brace which can be secured to the body in a stable and comfortable manner solely by use of arm and crotch straps.

6. The provision of frame members formed of radioluscent plastic enabling the cervical spine to be seen by X-ray or other body examining apparatus from all angles.

7. A brace construction which leaves the chest area free for cardiac monitoring and cardiac examination.

8. A mounting strap arrangment which can be quickly connected and disconnected in emergency situations.

9. A mounting configuration which does not require any securing means to be mounted directly over the breast area of the patient.

10. The provision of mounting at least some of the strap connectors on hinged supports so as to make wearing of the invention brace comfortable to the patient having large breasts or the obese patient.

11. A brace which permits cardiac massage during emergency transit.

12. A brace which permits the patient's arms and legs when not injured to remain mobile and unrestricted.

13. A brace which is easily installed by slipping under the back of the patient.

14. A brace which does not have to be removed for preliminary examinations in emergency room procedures.

15. A brace which can be easily removed in the emergency room with the patient in a supine position.

16. A brace which imposes no respiratory or cardiac restriction and permits ease of monitoring blood pressure, particularly during emergency transport.

What is claimed is:

1. An emergency transport neck immobilizing brace, comprising:
   (a) an integral rigid frame structure including:
      (i) a pair of laterally-spaced curved shoulder support frame portions formed to fit, be supported on, and be secured to the shoulders of a person's body;
      (ii) back frame portions extending from said shoulder support frame portions and forming open frame structure mountable behind and extending from the shoulders toward the pelvic region of said person's body; and (iii) open support frame structure extending outwardly from said shoulder support frame portions opposite to the direction of extension of said back frame portions and including side frame structure formed to reside on opposite sides of and spaced outwardly from the head of said person's body;

(b) strap and connector means on said frame structure providing straps of adjustable length and associated connectors mounted in a manner enabling said frame structure to be stably secured to the shoulders and other selected portions of said person's body with said shoulder support frame portions engaged with the shoulders of the person's body and said back frame portions engaged with the back of said person's body;

(c) a head halter assembly mounted on said support frame structure including:
(i) a chin-engaging head halter;
(ii) a pair of laterally spaced straps secured to opposite sides of said halter; and
(iii) a mechanism operatively associated with said pair of halter straps for placing in traction the head of the person's body employing said brace; and (d) a head-bracing assembly including a single pair of cushion means mounted on said side frame structure and adjustably engagable with opposite sides of the head of the person's body employing said brace in a manner effective to embrace the head for preventing lateral, forward and backward movement of the said person's head.

2. An emergency transport neck immobilizing brace, comprising:

(a) a first frame comprising a pair of inverted U-shaped frame members with top, front and back portions thereof held in laterally-spaced, substantially parallel positions by integrally-secured bars extending between the respective back portions of said first frame members;

(b) a second frame comprising a pair of inverted J-shaped frame members with top, front and back portions thereof held in laterally-spaced, substantially parallel positions by integrally-secured bars extending between the respective back portions of said second frame members, the top portions of said second frame J-shaped frame members being suitably curved and joined to and extending between the outer extremities of said first frame front and back portions for service as shoulder supports, the front and back portions of said second frame J-shaped frame members forming continuations of the respective front and back portions of said first frame U-shaped members to which the second frame J-shaped members are joined;

(c) a first pair of crotch-securing assemblies having a pair of crotch straps of adjustable length secured at one end to a back portion of said second frame and releasably engagable at the opposite end to mating connectors secured on other back portions of said second frame;

(d) a second pair of arm-securing assemblies having a pair of arm straps of adjustable length secured at one end to a back portion of said second frame and releasably engageable at the opposite end to mating connectors secured at selected positions on the front of a selected one of said frames;

(e) a head halter assembly comprising a head halter, a pair of straps supporting said halter, a support bar rotatably mounted on and extending between said first frame top portions and receiving said straps in laterally-spaced positions for winding thereon and a handle-operated ratchet mechanism for rotating said support bar to wind said straps on said support bar for placing the head of the person using said brace in traction; and (f) a pair of cushion assemblies on said first frame including cushion-mounting frames mounted for adjustable vertical, horizontal and angular positioning thereof and including cushion means securable in selected positions on opposite sides of the head of a person using said brace to substantially limit forward and backward and lateral movement thereof when in said brace.

3. A brace as claimed in claim 2 wherein said halter assembly includes a pair of springs supporting said halter enabling said halter to be tractioned under the tension of said springs.

4. A brace as claimed in claim 2 wherein said first frame front portions are slotted, said cushion-mounting frames are also slotted with slots matable with said first frame front portion slots and including fastener means mounted in said slots for adjustable securement of said cushion-mounting frames on said first frame.

5. A brace as claimed in claim 2 wherein said cushion means comprise a pair of cushions detachably secured to said cushion mounting frames by mating Velcro-type fastening means.

6. A brace as claimed in claim 2 wherein at least one pair of said mating connectors of said arm securing assemblies are mounted on outer extreme hinged portions of said first frame front portions.

7. A brace as claimed in claim 2 wherein each of said frame members are formed of radioluscent material.

8. An emergency transport neck immobilizing brace, comprising:

(a) a first frame formed of radioluscent material comprising a pair of inverted U-shaped frame members with top, vertically-slotted front and back portions thereof held in laterally-spaced, parallel positions by integrally-secured parallel, laterally-spaced crossbars extending between the respective back portions of said first frame members;

(b) a second frame formed of radioluscent material comprising a pair of inverted J-shaped frame members with top, front and back portions thereof held in parallel, laterally-spaced positions by integrally-secured, parallel-spaced crossbars extending between the respective back portions of said second frame members, the top portions of said second frame J-shaped frame members being suitably curved and joined to and extending between the outer extremities of said first frame front and back portions for service as shoulder supports, the front and back portions of said second frame J-shaped frame members forming continuations of the respective front and back portions of said first frame U-shaped members to which the second frame J-shaped members are joined;

(c) a first pair of crotch-securing assemblies having a pair of crotch straps of adjustable length secured at one end to the back portions of said second frame and releasably engagable at the opposite end to mating connectors secured on front portions of said second frame;

(d) a second pair of arm-securing assemblies having a pair of arm straps of adjustable length secured at one end to the back portions of said second frame and releasably at the opposite end to mating connectors secured at selected positions on the front of said frames, at least one pair of said mating connectors of said arm securing assemblies being mounted on outer extreme hinged portions of said first frame front portions;

(e) a head halter assembly comprising a head halter, a pair of spring-tensioned straps supporting said halter, a halter support bar rotatably mounted on and extending between said first frame top portions and receiving said straps in laterally-spaced positions for winding thereon and a handle-operated ratchet mechanism for rotating said support bar to wind said straps on said support bar for placing a person's head in traction when in said halter; and (f) a pair of cushion assemblies on said first frame including slotted cushion-mounting frames mounted in a manner enabling mating of the slots of said first frame with the slots of said cushion-mounting frames and fastener means in said slots for vertical and horizontal positioning thereof and including a pair of detachable cushion means securable in selected positions on opposite sides of the head of the person using said brace to substantially limit forward and backward and lateral movement thereof when in said brace.

* * * * *

UNITED STATES PATENT AND TRADEMARK OFFICE
CERTIFICATE OF CORRECTION

PATENT NO. : 4,632,099

DATED : December 30, 1986

INVENTOR(S) : Leonard J. Mollo and Oscar S. Cunanan

It is certified that error appears in the above-identified patent and that said Letters Patent is hereby corrected as shown below:

On the title page inventors should read

--(76) Inventors: Leonard J. Mollo, Rte. 1, Box 1,
Highway 20, Lumberbridge, N.C. 28357;
Oscar S. Cunanan, 102 Dunedin Court,
Cary, North Carolina 27511 --.

Signed and Sealed this

Twenty-eighth Day of April, 1987

Attest:

DONALD J. QUIGG

Attesting Officer

Commissioner of Patents and Trademarks